United States Patent [19]

Obenaus et al.

[11] 4,423,271
[45] Dec. 27, 1983

[54] PROCESS FOR PRODUCING HIGH PURITY ISOBUTENE BY DEHYDRATING TERTIARY BUTANOL

[75] Inventors: Fritz Obenaus; Bernd Greving, both of Marl; Heinrich Balke, Herten; Bernhard Scholz, Marl, all of Fed. Rep. of Germany

[73] Assignee: Chemische Werke Hüls AG, Marl, Fed. Rep. of Germany

[21] Appl. No.: 424,576

[22] Filed: Sep. 27, 1982

[30] Foreign Application Priority Data

Dec. 24, 1981 [DE] Fed. Rep. of Germany ....... 3151446

[51] Int. Cl.³ ............................................. C07C 5/22
[52] U.S. Cl. ................................... 585/639; 585/638
[58] Field of Search ............................... 585/638, 639

[56] References Cited

U.S. PATENT DOCUMENTS

| | | | |
|---|---|---|---|
| 3,510,538 | 5/1970 | Rosenthal | 585/639 |
| 3,629,478 | 12/1971 | Haunschild | 585/638 |
| 3,634,535 | 1/1972 | Haunschild | 585/638 |
| 4,165,343 | 8/1979 | Levine et al. | 585/638 |
| 4,232,177 | 11/1980 | Smith | 585/639 |
| 4,242,530 | 12/1980 | Smith | 585/510 |
| 4,313,016 | 1/1982 | Manning | 585/510 |
| 4,320,232 | 3/1982 | Volkamer et al. | 585/639 |
| 4,331,824 | 5/1982 | Ikeda et al. | 585/638 |

*Primary Examiner*—Curtis R. Davis
*Attorney, Agent, or Firm*—Wells & Wells

[57] ABSTRACT

Tertiary-butanol in an aqueous solution containing from 40 to 90 percent by weight of tertiary butanol in homogeneous and liquid phase is dehydrated at a fixed catalytic bed consisting of a strongly acidic ion exchange resin at a temperature from 80° to 150° C. and at a pressure from 5 to 25 bars for the purpose of producing isobutene by dehydrating tertiary butanol.

Thereupon the homogeneous, liquid reaction mixture is fractionated in a distillation sector separate from the reaction chamber, the isobutene being separated from the water and from the unreacted tertiary butanol. The unreacted tertiary butanol is returned as an aqueous solution in a circulating flow rate to the reactor under the conditions that the mixture of fresh-fed tertiary butanol and the circulating tertiary-butanol/water mix contains from 40 to 90 percent by weight of tertiary butanol at the reactor inlet.

5 Claims, 2 Drawing Figures

PROCESS FOR PRODUCING HIGH PURITY ISOBUTENE BY DEHYDRATING TERTIARY BUTANOL

CROSS-REFERENCE TO A RELATED APPLICATION

Applicants claim priority under 35 USC 119 for application P 35 51 446.4, filed Dec. 24, 1981, in the Patent Office of West Germany.

BACKGROUND OF THE INVENTION

The field of the invention is isobutene and the present invention is particularly concerned with the production of high-purity isobutene by dehydrating tertiary butanol (TBA) in the presence of a strongly acidic synthetic resin cation exchanger as the catalyst.

The state of the art of processes for producing isobutene by dehydrating TBA may be ascertained by reference to U.S. Pat. Nos. 2,377,026; 3,510,538; 3,665,048; 4,012,456; 4,036,905; and 4,155,945, and British Pat. No. 2,022,129, the disclosures of which are incorporated herein.

Ion exchange resins suitable in the present invention are disclosed in U.S. Pat. Nos. 2,480,940; 2,922,822; and 3,256,250, and British Pat. No. 957,000, the disclosures of which are incorporated herein.

TBA dehydration takes place reversibly and endothermally. The conversion into isobutene and water increases with rising temperature in the view of the chemical equilibrium.

Accordingly, in industry the TBA dehydration is predominantly carried out at high temperatures of about 180° to 450° C. in the presence of weakly acidic catalysts such as silica gel, thorium oxide, titanium(IV)-oxide or especially aluminum oxide as disclosed in U.S. Pat. Nos. 4,036,905; 3,665,048; and 2,377,026. While a high TBA conversion is achieved using high temperatures, the considerable losses in isobutene by its oligomerization on the other hand represent a drawback. In addition to isobutene oligomerization there also takes place an undesired isomerization of the formed isobutene to n-butenes as disclosed in U.S. Pat. Nos. 3,665,048, and 2,377,026, causing further product losses, more significantly however making the separation and extraction of pure isobutene especially disadvantageously difficult.

When the dehydration of TBA is carried out at lower temperatures (below 180° C.) more active and strongly acidic catalysts are needed. Due to their inherent drawbacks such as corrosion, waste water problems, costly recovery, etc., the homogeneous acid catalysts such as mineral acids, organic sulfonic acids and heteropoly acids drop in significance for the dehydration reaction. On the other hand, cation exchanger resins assume significance as catalysts.

Due to the poorer equilibrium conditions, only partial TBA conversions remain possible at lower temperatures. Therefore higher degrees of conversion require continuous removal of the reaction products.

This continuous removal is achieved by setting lower pressures of reaction below 2 bars, so that the isobutene distills off as a low boiling point component from the reaction mixture in continuous manner together with a partial-pressure determined by the proportion of TBA and water as disclosed in U.S. Pat. No. 3,256,250. As the rate of formation—which in any event is low—strongly drops as the water content in the reaction mixture increases, such procedures are only suitable for reaction mixture rich in TBA. Process steps have been described for TBA solutions which are richer in water, wherein inert entraining agents are proposed for the water of reaction as disclosed in U.S. Pat. Nos. 3,510,538 and 4,155,945. For instance when adding benzene or xylene as the entraining agent, there takes place however in the light of the teaching of U.S. Pat. No. 3,510,538 and especially above 100° C. a reinforced oligomerization of isobutene. Moreover, the addition of a third substance supporting the reaction, on the other hand, hampers reprocessing because this accessory substance must be discharged again and be recovered.

It has been suggested in order to overcome these drawbacks that the aqueous TBA solution be fed to the rectifier part of a column from which, preferably at 85° C. and a maximum pressure of 1.9 bars an aqueous vapor flow rich in TBA is driven through the catalytic bed mounted in loose bulk above the rectifier section as disclosed in U.S. Pat. No. 4,012,456. Together with the proportion of TBA and water, the isobutene is withdrawn in gaseous form from the reaction section. This method is satisfactory with regard to selectivity, but it does require a specially formed cation exchange resin not on the market.

In addition to the frequently complex reaction procedure, the prior art methods basically incur a substantial drawback:

Isobutene is obtained in gaseous form together with a partial-pressure determined proportion of TBA and water at a pressure no longer permitting it to condense using the conventional coolants used in industry.

The extraction of pure isobutene by rectification therefore requires costly compression and condensation stages. To avoid this drawback, the method of British Pat. No. 2,022,129 performs the dehydration of TBA in the presence of acid cation ion exchange resins at a pressure of at least 5 bars. The temperature is selected correspondingly to be so high that the produced isobutene can be removed in gaseous form together with the proportion of TBA and water from the reaction zone. Depending on the pressure of reaction, temperatures of about 180° C. or higher are required in this procedure, that is, these are temperatures above the limit of application of commercial cation exchange resins and from which therefore only a restricted catalyst life can be expected under these conditions. Moreover the higher temperatures entail a lesser isobutene selectivity compared to the previously cited methods. There is a common factor in all these procedures reflecting the state of the art for TBA dehydration in the presence of acid synthetic resin exchangers, namely that the components of reaction are present in a mixed phase consisting of a gaseous and a liquid phase, and that the catalyst is present as a third and solid phase. Thereby the mass transfer to the catalytically effective centers of the catalyst will be hampered, and as a result, the rate of isobutene formation referred to the reactor volume, i.e., the time-space-yield, is unsatisfactory for isobutene.

Accordingly, large amounts of catalyst are required to implement the process on an industrial scale. This causes problems regarding the apparatus to be used and the heat supply to the strongly endothermal splitting reaction, as heat from only a heat source of comparatively low temperature can be fed to the synthetic exchangers being used on account of the low temperature stability, as a result of which a large heat transfer area is required.

To improve the mass transfer conditions for splitting, the methods of the state of the art use a movable catalytic bed. The synthetic resin structure of commercial cation exchangers when used in polar substances such as TBA and water, experiences marked swelling and deformation substantially degrading the mechanical stability of the catalyst.

Therefore, it is impossible to prevent abrasion and fracture of the catalyst particles in a moving catalytic bed.

SUMMARY OF THE INVENTION

Having in mind the limitations of the prior art it is an object of the present invention to provide a process for the large-scale industrial production of high-purity isobutene by dehydrating TBA making it possible to dehydrate in a more efficient and more economical process using a simpler procedure.

According to the present invention tertiary-butanol in an aqueous solution containing from 40 to 90% by weight of tertiary butanol in homogeneous and liquid phase is dehydrated at a fixed catalytic bed consisting of a strongly acidic ion exchange resin at a temperature from 80° to 150° C. and at a pressure from 5 to 25 bars for the purpose of producing isobutene by dehydrating tertiary butanol.

Thereupon the homogeneous, liquid reaction mixture is fractionated in a distillation sector separate from the reaction chamber and the isobutene is separated from the water and from the unreacted tertiary butanol. The unreacted tertiary butanol is returned as an aqueous solution in a circulating flow rate to the reactor under the conditions that the mixture of fresh-fed tertiary butanol and the circulating tertiary-butanol/water mixture contains from 40 to 90% by weight of tertiary butanol at the reactor inlet.

BRIEF DESCRIPTION OF THE DRAWINGS

The drawings appended hereto are flow sheets showing.

DESCRIPTION OF THE PREFERRED EMBODIMENTS

Figure 1:
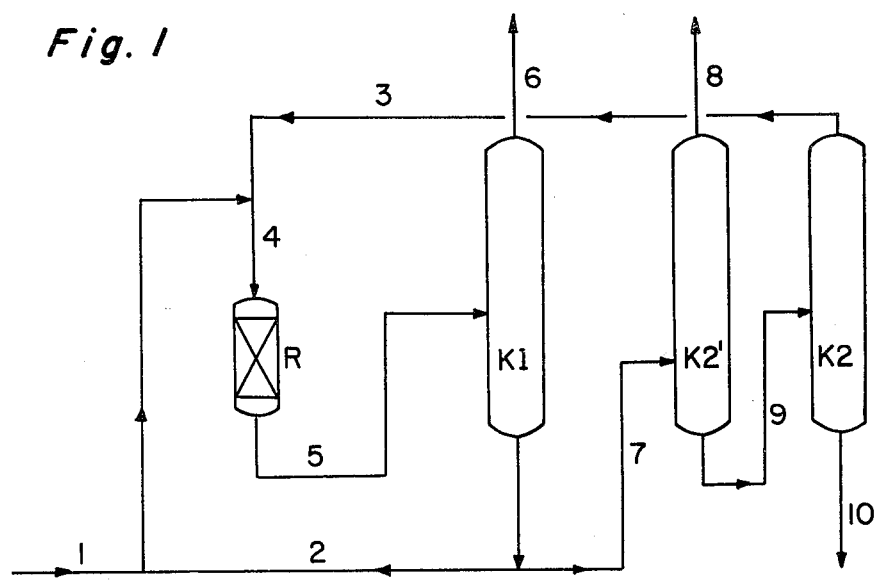
In FIG. 1 a preferred implementation of the process of the present invention.

Suitable input materials are both industrial TBA contaminated with isobutene oligomers, for instance diisobutene, and pure TBA. Preferably TBA-water mixtures are used such as the TBA-water azeotropes that are obtained in reprocessing by distillation.

Surprisingly the process of the present invention offers high-purity isobutene with a very high space-time-yield and with an isobutene selectivity of practically 100 mole-% provided the splitting or the back-splitting of TBA into isobutene and water is carried out with a strongly acidic organic ion exchanger mounted in a fixed bed and that it be performed in a homogeneous and liquid phase and that the homogeneous liquid discharge of reaction be fed to a distillation section where the isobutene and the water are separated from the unconverted TBA which is returned as an aqueous TBA solution to the dehydration stage. This was unexpected because West German Published Patent Application No. 2,913,976 discloses on page 20, lines 27 through 31 that at excessive pressure, that is, in the presence of a homogeneous liquid phase, it is difficult to obtain dehydration. Accordingly, it was surprising that the process of the present invention allows producing isobutene in a homogeneous liquid phase at these temperatures at heretofore unachieved space-time yields and selectivity.

The present invention offers another advantage in the separation between the reaction chamber and the isobutene processing, whereby a free and flexible choice is given regarding the optimal conditions for the reaction and distillation stages and this is a great advantage especially as regards both the product quality and the catalyst stability.

In the process of the present invention, the temperature of reaction is between 80° and 150° C. Adiabatic operation is advantageous at a raised temperature, for instance of 110° C. The preferred temperature is between 100° and 130° C., because both the catalyst life and the isobutene space-time-yield are economically optimal in this range.

The pressure of reaction is between 5 and 25 bars, the pressure being selected at such a level that the isobutene produced in the reactor will remain homogeneously dissolved in the reaction mixture without formation of a gas phase. As a rule it is advantageous that the pressure of reaction exceed the pressure of the column in the reprocessing part, as it is possible in this case to use the expansion evaporation to support advantageously the separation of the isobutene.

The TBA content in the input mixture prior to the reactor is between 40 and 90% by weight, preferably between 55 and 85% by weight. The input mixture introduced into the reactor consists of a supply of fresh tertiary butanol, preferably in the form of a TBA/water azeotrope, and of the circulating TBA/water mixture. This mixture is continuously introduced into the reactor.

The particular, especially advantageous space velocity (LHSV) depends on the water content of the mixture of reaction and to a high degree on the temperature of reaction and the activity of the catalyst used, and must be determined individually for each catalyst.

The liquid hour space velocity in liters of input per liter of swelled catalyst per hour at a temperature of reaction between 80° and 100° C. as a rule is between 50 and 100 liters/liter·hour, between 100° and 130° C. it is 100 to 300 liters/liter·hour and between 130° and 150° C. it is up to 600 liters/liter·hour.

However, less advantageous space velocities are also selectable. Control Example 1 of the present invention shows the lesser space-time-yield and the clearly degraded selectivity for a two-phase, liquid reaction mixture. Control Example 2 shows the increasingly degraded isobutene selectivity for a TBA concentration exceeding 90% by weight in the reaction mixture. Control Examples 3 and 4 show especially the lesser space-time-yield and the poorer selectivity for gaseous-liquid reaction mixtures from which the isobutene is withdrawn in gaseous form.

Sulfonated organic resins such as disclosed in U.S. Pat. No. 2,480,940, and in particular those sulfonated divinylbenzene-cross-linked polystyrene resins disclosed in U.S. Pat. No. 2,922,822—which may be gel-like in nature, or which may evince a sponge structure with macropores as disclosed in British Pat. No. 957,000 to enlarge the surface, or increase the hydrolysis stability of their catalytically effective sulfonic acid groups may comprise a halogenated synthetic resin structure as disclosed in U.S. Pat. No. 3,256,250 which are suitable as organic ion exchangers. The commercial organic ion exchangers are preferred in hydrogen form. However, commercial, macroporous cation exchangers modified by partial ion exchange or by thermal desulfonation may evince satisfactory activity with simultaneous higher hydrolysis stability of the sulfonic acid groups.

The pure production of isobutene and the removal of the water takes place in a processing section separate from the reaction chamber. FIG. 1 shows a preferred implementation of the process of the invention wherein the homogeneous liquid reaction mixture leaving the reactor is fed through line 5 to a pressurized column (K1) to produce pure isobutene.

The head pressure of column K1 as a rule is 3 to 10 bars, preferably 5 to 7 bars, because this range permits especially economical distillation when the distillate is condensed with a coolant.

The isobutene is distilled off through the head with traces of water corresponding to the water/isobutene azeotrope as shown by line 6 of the Figures. The water deposits in the receiver as a separate phase and can be removed in problem-free manner. The mixture of TBA and water accumulating at the bottom as a rule contains less than 0.5% by weight of isobutene and the main amount is returned through line 2 ahead of the reactor. The sump temperature can be so selected from the reactor input temperature that on one hand distillation can be carried out economically and on the other hand the temperatures required to maintain catalyst stability are not exceeded. Obviously lesser or higher pressures also may be applied in this distillation stage, even though they are less appropriate economically.

To separate the water produced in equivalent amounts with respect to the isobutene and any water entrained in the fresh TBA, a partial flow of the sump product is fed through line 7 to column K2' where the isobutene dimers contained in the input mixture or possibly produced during the reaction in trace amounts are distilled off through the head by line 8 as a ternary mixture with TBA and water. The sump product is fed through line 9 to column K2 from where a TBA/water mixture of azeotropic composition is removed as the head product and is fed back through line 3 to a position ahead of the reactor. The excess water in the sump of column K2 is evacuated through line 10. Columns K2' and K2 are operated at normal or higher pressures.

The ternary mixture from the head of K2' is appropriately decomposed with water and the aqueous phase containing TBA is returned to the column. If there are no isobutene dimers in the reaction mixture, column K2' is eliminated.

When a TBA/water azeotrope is used (about 88% by weight of TBA is normal pressure) as the fresh input mixture (line 1), the ratio of the circulating flow of the sump of column K1 to the flow from the head of column K2 is preferably 2:1 to 130:1, in particular 5:1 to 30:1.

The TBA/water mixture preferably is made to pass from top to bottom through the catalytic fixed bed of reactor R.

Figure 2:
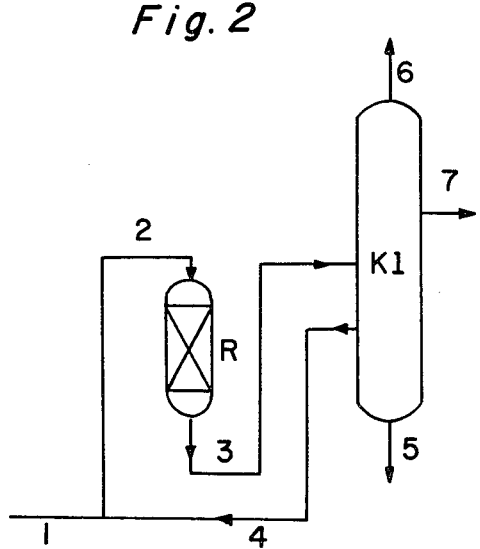
FIG. 2 shows another embodiment of the present invention which is especially economical.

Another embodiment of the process of the present invention, which is especially economical, is reproduced in FIG. 2 for elucidation.

In FIG. 2, the homogeneous liquid reaction discharge is fed through line 3 into the pressurized column K1 where the pure isobutene is distilled through the head in the form of the water azeotrope. The entrained water separates as a separate phase in the receiver. The TBA is azeotropically distilled from the draining water in the separation part of the column, whereby the water rid from TBA and isobutene is removed at the sump of the column K1 through the line 5. A TBA/water mixture enriched with TBA is tapped from an intermediate tray above the separation part as a side flow through line 4 and is mixed as a circulating flow with the fresh flow of the educt (line 1), whereupon it is made to pass preferably from top to bottom through line 2 through the reactor. If the reaction mixture contains isobutene oligomers, these can be evacuated by a side tap at the concentrating part of column K1 through the line 7.

This preferred embodiment of FIG. 2 of the process is especially economical because the condensation of the TBA/water azeotrope is eliminated in the separation of the water in a condenser of its own, for instance when using column K2, and in lieu thereof the heat of condensation serves to interrupt the energy-consuming reaction circulation.

The above described process permits producing in a simple manner high-purity isobutene from TBA with an isobutene selectivity in excess of 99.9 mole-%. The reaction rate of TBA amounts to practically 100%. Because the reaction is carried out under mold conditions at a catalytic fixed bed, even commercial organic cation exchangers offer industrially satisfactory catalyst lives. The reaction can be performed with continuous or batch-wise inputs of fresh TBA into the reaction circuit. Preferably the operation will be continuous. The purity of the isobutene so produced is in excess of 99.9%. As a rule values up to 99.99% are achieved. The residue is water. The high-purity isobutene of the invention so obtained is preferably used in preparing polyisobutene, butyl rubber and in alkylation.

The following examples elucidate the process, though they are not to be construed to limit it in any manner.

EXAMPLE 1

The catalyst used is a commercial, strongly acidic ion exchange resin (a macroporous, sulfonated divinylbenzene-cross-linked polystyrene resin). Further resin characteristics are: BET surface of about 40 $m^2/g$ of dry resin, divinylbenzene content about 18%, grain size distribution between 0.5 and 1.3 mm, hydrogen ion capacity about 3.8 mval $H^+/g$ of dry resin.

As shown in FIG. 1, 711 kg/h of fresh educt containing 623 kg/h of TBA, 85 kg/h of water and 2.84 kg/h $C_8$ olefins are passed through line (1) into the reactor R filled with 78 liters of the above-described cation exchange resin, and into this reactor are fed through line (2) 10,455 kg/h of circulation mixture returned from the sump of column K1 and containing 6,480 kg/h of TBA, 3,938 kg/h of water and 36.9 kg/h of $C_8$ olefins, and through line (3), 565 kg/h of circulation mixture from the head of the column K2, containing 497 kg/h of TBA and 68 kg/h of water, and a total through line (4) of 11,731 kg/h of input mixture containing 64.7% by weight of TBA.

The splitting reaction is carried out at 10 bars and at an average temperature of 120° C.

The reaction mixture is made to pass through the line 5 into the column K1 and is expanded prior to entry to the 6 bar column pressure (≙ head pressure). 470 kg/h of pure isobutene are evacuated from column K1 through its head (line 6). The distillate contains water corresponding to the azeotrope which settles as a separate phase in the receiver and is evacuated.

The composition of the sump product of column K1 is 6,980 kg/h of TBA, 4,242 kg/h of water and 39.75 kg/h of $C_8$ olefins. The main amount is returned through the line (2). A partial flow of 806 kg/h is fed through the line (7) following expansion to the column pressure of 1.2 bars ($\triangleq$ head pressure) to the column K2'. 2.85 kg/h of $C_8$ olefins together with 2.2 kg/h of TBA and 0.65 kg/h of water are removed from the column K2' through its head (line 8) as a ternary mixture. The sump product is fed through line (9) to the column K2 where the azeotropic TBA/water mixture is evacuated through the head (head pressure is 1.02 bars) and is returned through the line (3). The ratio of the circulating flow of column K1 to the flow of column K2 is 18.5:1. 235 kg/h of water accumulate in the sump of the column K2 and are evacuated through the line (10). The isobutene selectivity practically is 100%. When decomposing the $C_8$/TBA/water mixture from the head of column K2' with water and returning the aqueous phase containing TBA, the reaction rate of TBA also practically is 100%. The purity of the isobutene is 99.99%.

EXAMPLE 2

The catalyst used is a commercial, strongly acidic ion exchange resin (macroporous, sulfonated divinylbenzene-cross-linked polystyrene resin) with the following characteristics: BET surface is about 25 m$^2$/g of dry resin, the divinylbenzene content is about 8%, the grain size distribution is between 0.5 and 1.2 mm, the hydrogen ion capacity is about 4.1 mval H+/g of dry resin.

According to the flow sheet of FIG. 2, the TBA splitting is carried out at an average temperature of 120° C. and a pressure of 20 bars as described below.

A reactor R is filled with 42 liters of the above described catalyst and receives the flow (2) containing 4,161 kg/h of TBA, 1,040 kg/h of water and 3.4 kg/h of $C_8$ olefins. The flow (2) contains 80% by weight of TBA and is composed of the fresh input (line 1) of 675 kg/h of TBA, 92 kg/h of water and 2.8 kg/h $C_8$ olefins and of circulating flow returned from the pressurized column K1 through the line 4 and containing 3,486 kg/h of TBA, 948 kg/h of water and 0.6 kg/h of $C_8$ olefins. The circulating flow returned through the line 4 contains 78.6% by weight of TBA. The reactor discharge is fed through line 3 into the column K1 and is expanded to the column pressure of 7 bars ($\triangleq$ head pressure). 510 kg/h of pure isobutene are distilled off in column K1 through the head (line 6). The distillate contains water according to the azeotrope, which is removed as a separate phase in the receiver. 256 kg/h of water arrive in the sump and are evacuated through line 5. 2.9 kg/h of $C_8$ olefins together with 2.5 kg/h of TBA and 0.7 kg/h of water are evacuated from the concentrating part of the column K1 through a side tap. Using the water from the head product receiver and part of the water evacuated from the sump, the TBA/water/$C_8$ olefin mixture is decomposed and the aqueous phase containing TBA is fed back. The circulating flow is tapped off sideways from the separation part of column K1 through the line 4 and is fed back to ahead of the reactor. The isobutene selectivity is 99.98%, the reaction rate for TBA is practically 100% and the isobutene purity is 99.99%.

EXAMPLES 3 THROUGH 8

TBA is dehydrated in a series of further examples by the procedure of Example 1 (see FIG. 1). The commercial, macroporous, strongly acidic ion exchange resin (sulfonated, divinylbenzene-cross-linked polystyrene resin) used as catalyst has the following characteristics: BET surface is about 35 m$^2$/g of dry resin, divinylbenzene content is 10%, grain size distribution is between 0.5 and 1.2 mm, the hydrogen ion capacity is about 4.5 mval H+/g of dry resin. 100 ml of this resin are made to swell in a TBA/water azeotrope (about 12% by weight of water) and filled into the lower quarter of a tubular reactor 100 cm long (inside diameter=2.29 cm) which is provided with a heating jacket. The residual volume is filled with V4A packings and acts as the preheating zone. A thermocouple is arranged in centrally displaceable manner within the reactor. Viewing windows to monitor the homogeneity of the liquid mixture was provided ahead and behind the reactor. The volume of the column sump of columns K1, K2' and K2 is kept constant by an automatic level control. A fresh azeotropic mixture of TBA and water that is free of isobutene oligomers is supplied through the line 1. Table 1 below lists the conditions applied and the results obtained. The space velocity (LHSV) is listed in liters of supply per liter of swollen catalyst per hour, the isobutene space-time-yield is indicated in kg of isobutene per liter of swollen catalyst per hour. The analysis of mass flows is performed by gas chromatography. Except for Example 5, column K2' is superfluous. The isobutene obtained is 99.99% pure.

Table 1 follows.

TABLE 1

| Example | Temperature °C. | Fresh azeotrope kg/h | LHSV l/l·h | Ratio of mass flows 1: | 2: | 3 | flow 4 TBA % by weight | % by weight H$_2$O | Space-time yield kg/l·h | Isobutene selectivity Mole-% |
|---|---|---|---|---|---|---|---|---|---|---|
| 3 | 110 | 0.39 | 54 | 1 | 9.3 | 1 | 70 | 30 | 2.6 | 100 |
| 4 | 110 | 0.69 | 140 | 1 | 15.5 | 1.1 | 70 | 30 | 4.6 | 100 |
| 5 | 120 | 0.44 | 45 | 1 | 6.5 | 0.9 | 70 | 30 | 2.9 | 99.9 |
| 6 | 120 | 1.02 | 139 | 1 | 8.2 | 1.3 | 70 | 30 | 6.8 | 100 |
| 7 | 120 | 0.48 | 80 | 1 | 12.6 | 0.6 | 60 | 40 | 3.2 | 100 |
| 8 | 120 | 1.0 | 206 | 1 | 16.0 | 0.6 | 60 | 40 | 6.5 | 100 |

EXAMPLE 9

The commercial cation exchange resin of Example 1 is used as the catalyst. A steel tubular reactor 80 cm long and 2.29 cm in inside diameter, provided with a casing acting as a thermostat provided with two zones which can be raised to different temperatures is filled with 20 ml of TBA/water azeotrope swollen exchange resin. The resin is located in the lower third of the reactor. The residual reactor volume is filled with V4A packings and acts as the preheating zone. A displaceable thermocouple is arranged centrally in the reactor. A viewing window arranged ahead and behind the reactor permits monitoring the homogeneity of the liquid mixture. The TBA splitting is carried out in a series of tests in nearly isothermal manner (the temperature differential in the catalytic bed is no more than 2° C.) following the procedure of Example 2, however, at a pressure of 11 bars, the temperature and the TBA concentration being varied in the mass flow 2. The fresh TBA is introduced through line 1 as pure (99%) TBA free from isobutene oligomers. The TBA concentration in the sideways tap of the output section of the column (line 4) is about 58% by weight for 60% by weight of TBA in the flow 2, about 68% by weight for 70% by weight of TBA, about 78% by weight for 80% by weight of TBA, about 85% by weight for 90% by weight of TBA. The mass flows are analyzed by gas chromatography. Table 2 lists the conditions applied and the results obtained. The definition in Examples 3 through 8 applies to the space velocity (LHSV) and the time-space-yield.

Table 2 follows.

TABLE 2

| Temperature °C. | Space velocity 1/l · h | Isobutene space-time yield (kg/l · h) for TBA % by weight in flow 2 | | | | Isobutene selectivity (Mole-%) for TBA % by weight in flow 2 | | | |
| --- | --- | --- | --- | --- | --- | --- | --- | --- | --- |
| | | 90 | 80 | 70 | 60 | 90 | 80 | 70 | 60 |
| 90 | 120 | | 2.0 | 1.4 | 1.0 | | 100 | 100 | 100 |
| 100 | 120 | | 4.1 | 3.0 | 2.2 | | 100 | 100 | 100 |
| 116 | 120 | | 7.3 | 6.0 | 4.8 | | 100 | 100 | 100 |
| 120 | 120 | | 15.1 | 12.0 | 9.8 | | 99.9 | 100 | 100 |
| 130 | 300 | | 22.6 | 19.2 | 15.3 | | 99.9 | 99.9 | 100 |
| 140 | 300 | 40.5 | | | | 99.8 | | | |

Isobutene purity is 99.99%

EXAMPLE 10

A macroporous ion exchange resin with the characteristics stated in Example 1 is so deactivated using 1 mmole/g of dry resin Na ions that a residual hydrogen ion capacity of 2.8 mval H$^+$/g of dry resin remains.

30 ml of resin swollen in a TBA/water azeotrope are filled into the reactor described in Example 9. The dehydration is carried out by the procedure described in Example 9. The conditions and the results obtained are listed in Table 3.

TABLE 3

| Temperature | LHSV 1/l · h | Isobutene time-space-yield (kg/l · h) at TBA % by weight in flow 2 | | |
| --- | --- | --- | --- | --- |
| | | 90 | 70 | 60 |
| 100 | 100 | | 2.5 | 1.9 |
| 110 | 120 | | 5.2 | 4.1 |
| 120 | 130 | | 10.5 | 9.2 |
| 140 | 300 | 28.3 | | |

CONTROL EXAMPLE 1

This example shows the activity and the selectivity of the catalyst resin in a two-phase liquid reaction mixture. The catalyst and the test procedure correspond to the data in Examples 3 through 8. For an average reaction temperature of 130° C., a reaction pressure of 15 bars and a space velocity of 120 liters/liter·hour, 0.16 kg/h of fresh azeotrope are made to pass in the line 1, together with the circulating flows from lines 2 and 3, through the reactor from top to bottom. The ratio of the mass flows from lines 1, 2 and 3 is 1:64.5:0.12. The TBA/water mixture at the reactor intake contains 25% by weight of TBA and 75% by weight of water. The reactor discharge is two-phase and liquid. The isobutene time-space-yield is 1.1 kg/liter·hour, the isobutene selectivity is 97.8 mole-%.

CONTROL EXAMPLE 2

In accordance with the procedure described in Example 9,—FIG. 2—a TBA/water mixture with 95% by weight of TBA and 5% by weight of water is made to pass in line 2, through the reactor at 150° C., a space velocity of 120 1/l·h and a pressure of reaction of 15 bars. The reaction discharge is homogeneous and liquid. The isobutene time-space-yield is 21.6 kg/l·h the isobutene selectivity is 98.6 mole-%.

CONTROL EXAMPLES 3 AND 4

The procedure of Example 2 is followed, except for the modifications below: 100 ml of cation exchange resin from Example 1, swollen in a TBA/water azeotrope, are in loose bulk in an 80 cm long glass reactor (4.5 cm inside diameter) with a displaceable thermocouple at the center and with a heating jacket. The pressure of reaction is selected in such a manner that the reaction mixture will boil at the particular reaction temperature. The fresh TBA/water mixture free of isobutene oligomers and azeotropic in nature is admixed with the circulating TBA/water mixtures and made to pass through the reactor from bottom to top. The turbulence caused thereby and by the evaporation of the formed isobutene keeps the catalyst dispersed. The formed isobutene is continuously removed in gaseous form through a bubble tray column (10 trays) located at the reactor head. The liquid phase of reaction is evacuated at the upper reactor end from the reactor volume (1.2 liters) through a filter cartridge and is treated similarly to the procedure described in Example 2. Table 4 shows the conditions applied and the results obtained. The space velocity and the time-space-yield always refer to the swollen catalyst volume. The mass flows were analyzed by gas chromatography.

TABLE 4

| Control Example | Temperature °C. | Reaction pressure bar | LHSV 1/l · h | % by weight in the flow isobutene ahead of the reactor | | space-time-yield kg/l · h | selectivity Mole-% |
| --- | --- | --- | --- | --- | --- | --- | --- |
| | | | | TBA | H$_2$O | | |
| 3 | 80 | 1.05 | 90 | 80 | 20 | 0.32 | 99.7 |
| 4 | 90 | 1.4 | 110 | 80 | 20 | 0.75 | 99.5 |

What we claim is:

1. A process for producing high-purity isobutene by dehydrating tertiary butanol in the presence of an acid catalyst, comprising:
(a) continuously feeding an aqueous solution containing from about 40 to 90 percent by weight of tertiary butanol into a reactor and dehydrating in a homogeneous and liquid phase at a fixed catalyst bed consisting of a strongly acidic ion exchange resin at a temperature from about 80° to 150° C. and a pressure of about 5 to 25 bars;

(b) fractionating the homogeneous, liquid reaction mixture in a distillation part separate from the reaction chamber and separating isobutene from the water and from the unreacted tertiary butanol; and (c) concentrating the unreacted tertiary butanol by distillation and feeding back a first portion of the mixture of water and unreacted tertiary butanol from step (b) to step (a), and discharging a second portion of said mixture at a rate sufficient to remove excess water.

2. The process of claim 1, wherein said second portion of said mixture of water and unreacted tertiary butanol discharged by step (c) is distilled to concentrate the unreacted tertiary butanol, and said concentrated unreacted tertiary butanol is recycled to step (a), and excess water is discharged as a bottom product.

3. The process of claim 1, wherein the tertiary butanol of step (a) is dehydrated at a temperature from about 100° to 130° C.

4. The process of claim 3, wherein the entire mixture of tertiary butanol and water at the reactor intake of step (a) contains from 55 to 85% by weight of tertiary butanol.

5. The process of claim 2, wherein said isobutene of step (b) is separated from the water/tertiary butanol mixture through the head of a distillation column, step (c) is executed from an intermediate tray below the feed flange of said column, said first portion of the mixture of water and the unreacted tertiary butanol being fed back to step (a) and said second portion of this mixture containing excess water flowing down to a separation section of the same column located between the bottom, where the excess water is discharged, and said intermediate tray, to which the unreacted tertiary butanol is distilled azeotropically for recycle to step (a).

* * * * *